Figure 1:
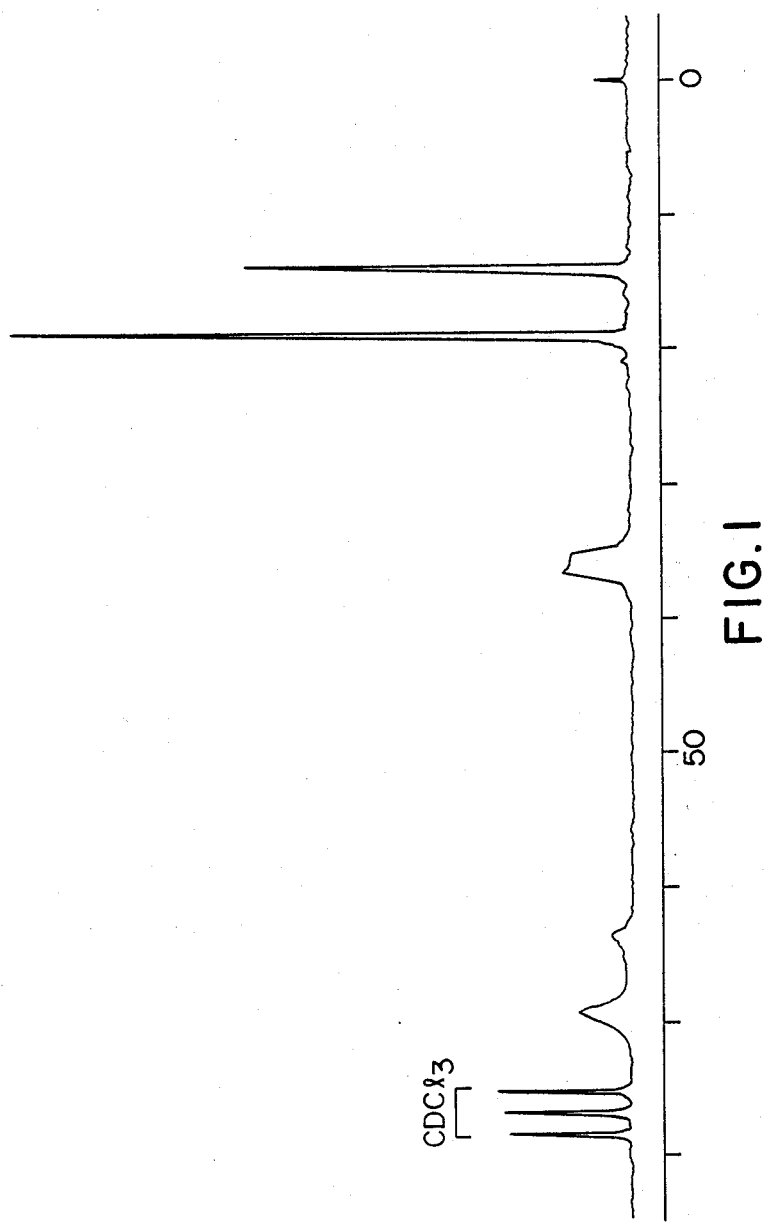

United States Patent [19]

Horns et al.

[11] Patent Number: 4,891,439
[45] Date of Patent: Jan. 2, 1990

[54] ALCOHOL-FREE ORTHOESTERS OF ZIRCONIUM AND HAFNIUM AND METHOD FOR THE PREPARATION THEREOF

[75] Inventors: Udo Horns, Rheinfelden; Hans-Günther Srebny, Stolzenau; Hans-Joachim Yahlensieck, Wehr, all of Fed. Rep. of Germany

[73] Assignee: Huels Troisdorf AG, Cologne, Fed. Rep. of Germany

[21] Appl. No.: 217,643

[22] Filed: Jul. 12, 1988

[30] Foreign Application Priority Data

Jul. 17, 1987 [DE] Fed. Rep. of Germany ....... 3723713

[51] Int. Cl.$^4$ .............................................. C07F 7/00
[52] U.S. Cl. ................................................... 556/54
[58] Field of Search ........................................ 556/54

[56] References Cited

U.S. PATENT DOCUMENTS 3,721,689  3/1973  Bardinet ................................. 556/54
3,752,834  8/1973  Bardinet et al. ...................... 556/54
3,754,011  8/1973  Hoch ..................................... 556/54

OTHER PUBLICATIONS

Journal of the Chemical Society, pp. 2025–2030 (1953) by J. Bradley.

Primary Examiner—John Doll
Assistant Examiner—Stuart L. Hendrickson
Attorney, Agent, or Firm—Felfe & Lynch

[57] ABSTRACT

Disclosed are very pure zirconium and hafnium orthoesters and a method for their preparation. In this method the reaction between the halides of these metals and the alcohols is performed in the presence of hydrocarbons or chlorinated hydrocarbons, and the alcohol is not use in excess. The obtained orthoesters are in very pure form and not as addition products with alcohol. They can be isolated as solids.

4 Claims, 7 Drawing Sheets

ALCOHOL-FREE ORTHOESTERS OF ZIRCONIUM AND HAFNIUM AND METHOD FOR THE PREPARATION THEREOF

BACKGROUND OF THE INVENTION

The subject of the present invention is alcohol-free orthoesters of zirconium and hafnium, and also a method for the preparation of the alcohol-free orthoesters of these metals. The preparation of zirconium and hafnium alkoxides, which are also called zirconic or hafnic acid esters is generally performed like the production of titanic acid esters by the reaction of the corresponding metal halides with alcohols. The alcohol that is used serves simultaneously as a solvent for the reaction and for the ester that forms, which is generally used in this solution. The halogen hydride that is released by this reaction is neutralized by the addition of amines.

The resulting products from that procedure contain a considerable polymer content in the form of metal oxane compounds which are produced substantially on the basis of the following secondary reactions.

The alcohol that is put in reacts with the evolving halogen hydride to form alkyl halide and/or alkenes and/or ethers; water is released which in turn has a hydrolyzing action on the metal ester to form metal oxane.

It has furthermore been found that, in the reaction of zirconium or hafnium tetrahalide with excess alcohol, and also in the transesterification of low zirconic or hafnic esters with higher alcohols, a product forms which has a higher molecular weight than corresponds to the formula $M(OR)_4$ ($M = Zr$ or $Hf$). Studies have shown that this product has one more molecule of the alcohol than corresponds to the formula $M(OR)_4$ ($R$ = alcohol moiety), although this product has also been called a zirconic or hafnic acid ester of the formula $M(OR)_4$ This known product, containing excess alcohol, is in a dimeric or oligomeric form, is a liquid and has been useable heretofore in all applications of zirconic and hafnic acid esters. However, this bound alcohol interferes in special applications, as for example when the known product is used as a catalyst in Ziegler/Natta polymerization reactions.

The object therefore was to prepare alcohol-free esters of zirconic and hafnic acid, and to devise a method for preparing these esters, in which the alcoholic esters would not form and the formation of polymers is lower in comparison to the known methods.

The Invention

To achieve this object a method has now been found for the preparation of zirconic and hafnic orthoesters of the formula I $$M(OR)_4 \quad (I)$$

in which M represents zirconium or hafnium and R represents an alkyl or cycloalkyl moiety of 1 to 20 carbon atoms, in which metal halides are reacted with alcohols and the neutralization is performed by means of amines, wherein the reaction is performed in a hydrocarbon or chlorinated hydrocarbon and the amount of alcohol used corresponds to the amount that is stoichometrically necessary for the formation of the orthoester.

The hydrocarbons and chlorinated hydrocarbons can be virtually any compounds of this group which are liquid in the reaction temperature range. They include, for example, the pentanes, hexanes, heptanes, isooctane, cyclohexane, methylcyclohexane; benzine fractions such as petroleum ether or ligroin, benzene, toluene, the xylenes, methylene chloride, chloroform carbon tetrachloride, trans-dichloroethylene, trichloroethylene, perchloroethylene, chlorobenzene, the dichlorobenzenes, trichlorotrifluoroethylene and 1,1,1,3-tetrachloropropane.

From this listing it appears that both aliphatic and aromatic or cycloaliphatic, chlorinated or unchlorinated hydrocarbons are suitable. The hydrocarbons may be branched, and can also have inert substituents.

The metal halides useable as starting products for the method according to the invention, such as $ZrCl_4$, $ZrBr_4$ or $HfCl_4$ need not be soluble in the useable solvents. For the reaction according to the invention it is sufficient that the metal halides be suspended in these solvents and be kept distributed therein during their reaction with the alcohols by stirring or other appropriate measures.

The alcohols suitable for use in the reaction include both aliphatic and cycloaliphatic, straight-chain or branched alcohols of 1 to 20 carbon atoms. Ether alcohols containing up to 10 ether bridges also can be reacted according to the invention.

The amount of alcohol used is chosen so that the desired metal tetraalkoxide is formed. The molar ratio of alcohol to metal halide is therefore around 4:1. A slight excess of alcohol, amounting to up to 10%, does not substantially interfere with the course of the reaction according to the invention. It is possible to use less than a stoichiometric amount of alcohol with respect to the metal halide, corresponding to the above-stated 4:1 molar ratio, but this reduces the yield of orthoesters with respect to the input metal halide.

The feeding in of the metal halide and alcohol can be performed in any desired manner, assuming that the stated molar ratio of the reactants is assured. Preferably, therefore, the alcohol is introduced into a suspension of the metal halide in the solvent according to the invention. Both components, however, can be introduced into a reactor simultaneously. It is advantageous to proportion the alcohol so that it virtually does not come into contact with the gas phase and is introduced under the surface of the reaction medium. This can be performed, for example, by introducing it into the reaction medium through a tube submerged in the solvent.

The products that form in the reaction between metal halide and alcohol are only partially soluble in the solvent. The reaction products decompose, however, in the neutralization with the amines, with the formation of the orthoester according to the invention and of alcohol which reacts with the still-unreacted metal halide, with the formation of the desired ester.

The addition of the amine can therefore be performed at any time during the entire reaction. Preferably, the amine is not added until after the feeding in of the alcohol. It is then advantageous to evacuate the reaction vessel and introduce the amine into the pressurized reaction vessel.

The amount of added amine depends on the amount of halogen hydride to be neutralized. The formed amine halide is insoluble in the solvent and is separated from the orthoester in a manner known in itself.

A preferred amine for use in the invention is ammonia. However, any other amine useful for binding and neutralizing halogen hydride is suitable. Other such amines include, for example, methylamine, ethylenediamine and pyridine.

The isolation of the orthoester from the solution in the solvent according to the invention is performed in a manner known in itself, preferably by distilling out the solvent. The then obtained orthoester contains no bound alcohol beyond the molar ratio of 1:4 of metal to alcohol, as has been proven by $^1$H NMR and $^{13}$C NMR measurements. as has been proven by These measurements also prove the structure of the new zirconic and hafnic esters according to the invention. In contrast to the known products, these esters are not in associated form, but correspond to the formula M(OR)$_4$ These new esters are solids above $-33°$ C. In contrast to the previously known yellow to brown ester adducts, they are colorless or only faintly colored. In the abovedescribed method of preparation they are produced in a purity that is sufficient for most applications. Further purification by known methods is possible.

For products which are solid in the aggregate under normal conditions, the common methods of solid processing by crystallization, in a crystallizer for example, or phase separation, for example by sedimentation or filtration, and drying, can be used. Some of the products according to the invention are not solid until after such additional treatment.

The reaction between metal halide and alcohol is generally performed at standard pressure. The use of a partial vacuum is also possible, especially when it is desired to accelerate the removal of the halogen hydride that forms while the alcohol is being fed in. Also the application of pressure is possible, especially after the addition of the amine.

The method according to the invention is best performed in practice in a normal stirrer reactor with a reflux condenser, under anhydrous conditions of course, by introducing the zirconium or hafnium halide in the reactor together with a suitable suspension medium and then feeding the alcohol in through a tube submerged beneath the surface of the stirred suspension.

This first part of the reaction is exothermic, the temperature in the reactor rising to 40° to 60° C.

After the alcohol is introduced into the suspension of metal halide and solvent, the gas space above the reaction medium is evacuated, preferably to a pressure of 150 mbar; the temperature in the stirring reactor then drops to 20° to 30° C. The reactor is filled with ammonia up to a pressure of about 1200 mbar. The reaction vessel is advantageously cooled with water or icewater during the neutralization. The temperatures in the reaction medium are between 3° and 60° C.

Following neutralization, the precipitated ammonium halide is filtered out and the solvent is distilled out of the filtrate.

Secondary reactions are thoroughly suppressed by this procedure so that the yields of pure product of general formula I amount to virtually 100%.

EXAMPLES

The following Examples will explain the invention without restricting its scope.

EXAMPLE 1

The reaction apparatus consisted of a 2000 ml multi-necked flask with internal thermometer, stirrer, dropping funnel with submerged tube and a reflux condenser.

204 g of ZrCl$_4$ was suspended in 750 g of heptane. 265 g of n-butanol was added to the suspension with stirring, over a period of 15 minutes, through a tube submerged below the surface of the reaction liquid. The internal temperature rose to 50° C. Two phases formed, each was colorless and turbid. Then the apparatus was evacuated down to 100 mbar absolute, and 64 g of NH$_3$ was introduced in gaseous form for 30 minutes until the pressure rose to ambient pressure. During the neutralization the reaction vessel was cooled with icewater. Removal of the NH$_4$Cl yielded 1055 g of clear filtrate. From this, after distilling out the heptane on the rotary evaporator, 330 g was obtained of 98% colorless, highly viscous Zr(O-n-C$_4$H$_9$)$_4$. M.P.: 134° C. The $_{13}$C NMR spectrum is shown in FIG. 1.

EXAMPLE 2

In a reaction apparatus as described in Example 1, 136 g of ZrCl$_4$ was suspended in 600 g of heptane. To this was added 142 g of isopropanol through the tube submerged below the surface of the reaction mixture over a period of 15 minutes, with stirring. The internal temperature rose to 52° C. Two phases developed, the lower one yellow and turbid, and the upper nearly colorless and turbid. Then the apparatus was evacuated to 200 mbar absolute, and 41 g of ammonia in gas form was introduced over a period of 26 minutes until the pressure rose to ambient pressure. During the neutralization the reaction vessel wa cooled with icewater. Separation of the NH$_4$Cl by a known method yielded 770 g of clear filtrate. From this 187.4 g of 98% Zr(O-i-C$_3$H$_7$)$_4$ in the form of a colorless, crystalline solid was obtained after distilling out the heptane on the rotary evaporator. Melting point: 208° C.

EXAMPLE 3

Figure 2:
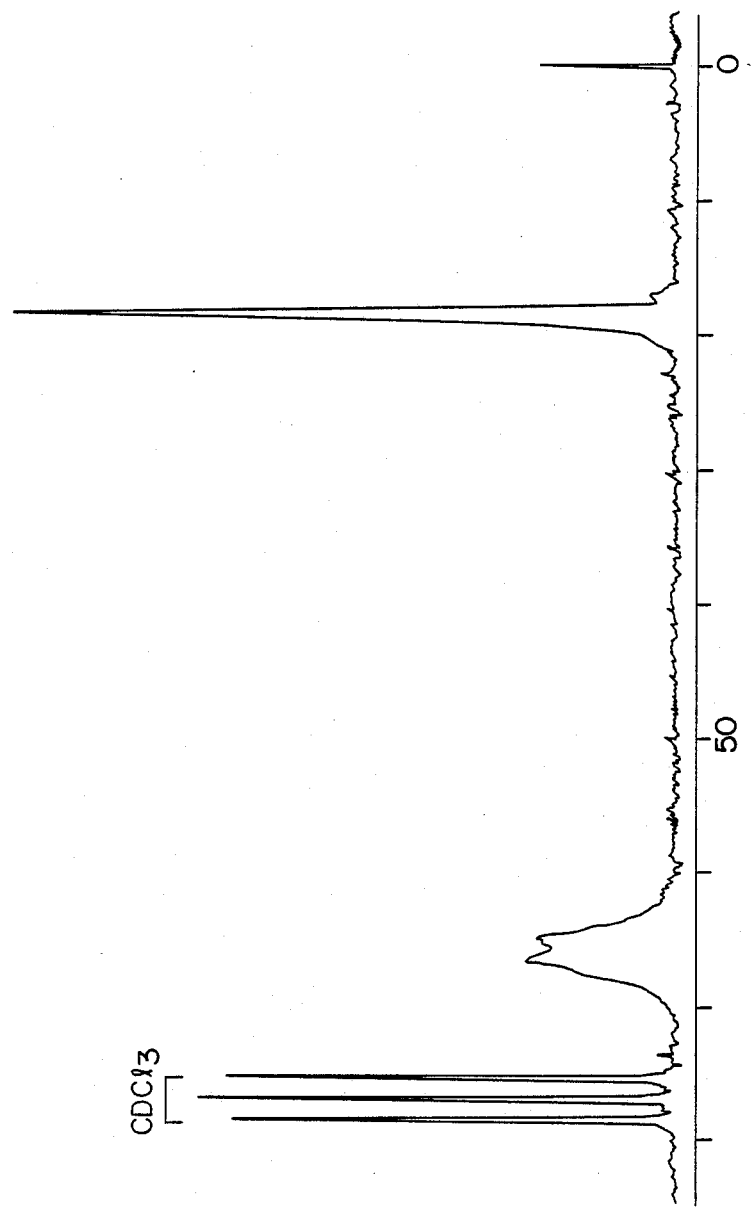

In a reactor as described in Example 1, 204 g of ZrCl$_4$ was suspended in 750 g of hexane. To this was added 169 g EtOH through the tube under the surface of the reaction mixture, over a period of 15 minutes, with stirring. The internal temperature rose to 51° C. Two phases formed, the lower one yellowish and turbid, the upper one colorless and turbid. Then the apparatus was evacuated to 150 mbar absolute, and 62 g of ammonia in gas form was introduced over 15 minutes until the pressure increased to ambient pressure. During the neutralization the reaction vessel was cooled with icewater. Separation of the NH$_4$Cl in a known manner yielded 971.3 g of clear filtrate. From this 232.7 g of 98% Zr(O-C$_2$H$_5$)$_4$ was obtained as a colorless, crystalline solid, after distillation on the rotary-evaporator. Melting point: 180° C. The $^{13}$C NMR spectrum is shown in FIG. 2.

EXAMPLE 4

Figure 3:
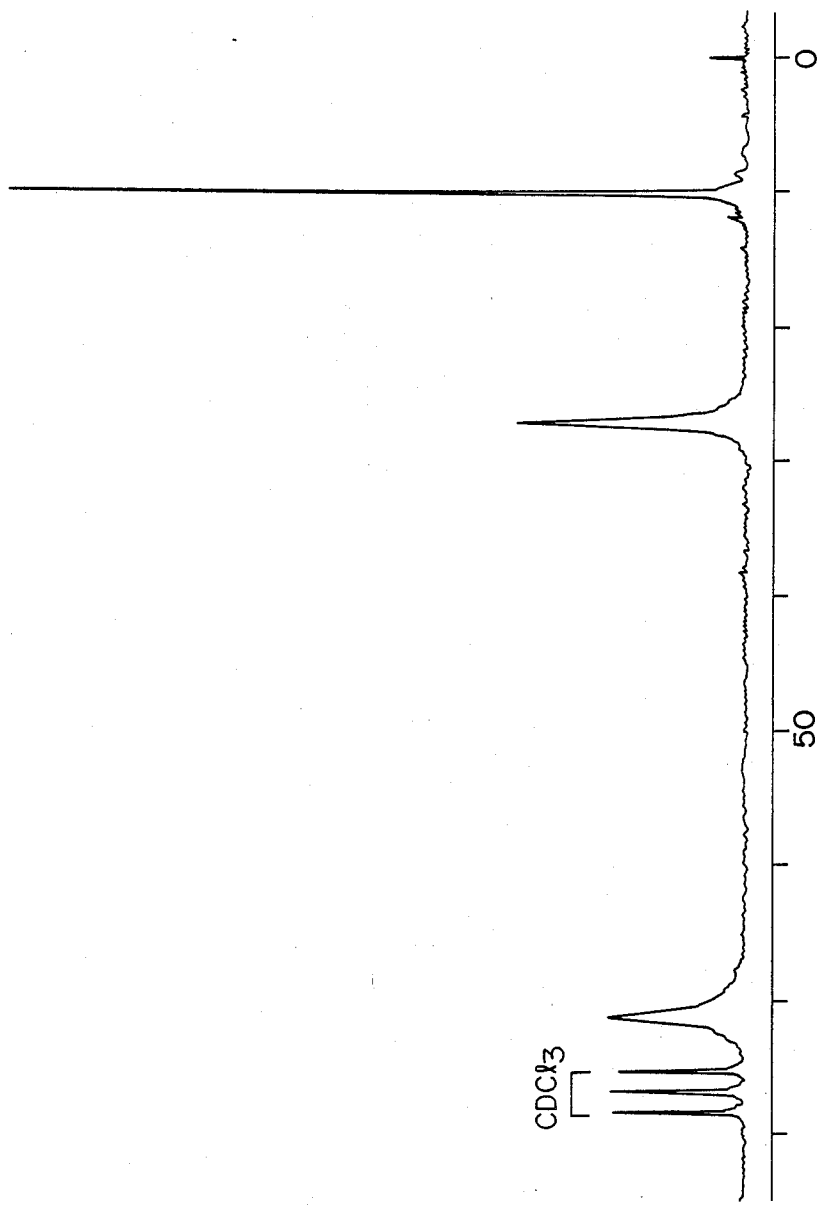

In a reactor as described in Example 1, 204 g of ZrCl$_4$ was suspended in 750 g of hexane. To this 220 g of n-propanol was added, with stirring, over 1 minute, through the tube submerged beneath the surface of the reaction mixture. The internal temperature rose to 51° C. Two phases formed: the bottom one yellowish and turbid, the upper one colorless and turbid. Then the apparatus was evacuated to 150 mbar absolute and 61 g of NH$_3$ was introduced in gas form over 32 minutes. During the neutralization the reaction vessel was cooled with icewater. Separation of the NH$_4$Cl in a known manner yielded 1020.3 g of clear filtrate. From this, after distillation on the rotary evaporator, 280.7 g was obtained of 98% Zr(O-n-C$_3$H$_7$)$_4$ as a colorless, crystalline solid. Melting point: 214° C. The $^{13}$C NMR spectrum is shown in FIG. 3.

EXAMPLE 5

Figure 4:
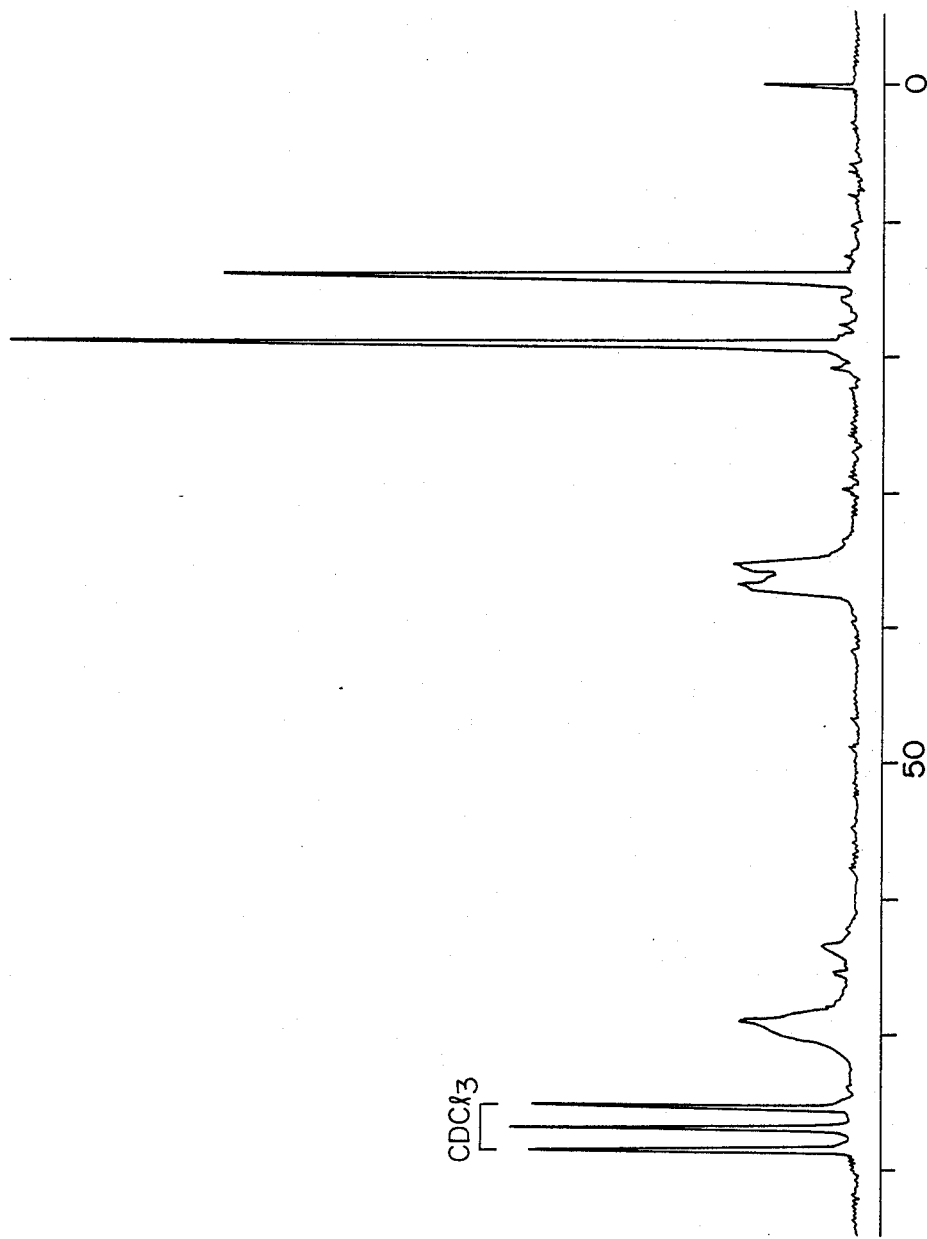

In a reactor as described in Example 1, 160 g of HfCl$_4$ was suspended in 600 g of heptane. To this 155 g of n-butanol was added with stirring over 15 minutes through the tube submerged below the surface of the reaction mixture. The internal temperature rose to 48° C. Two phases developed, both colorless and turbid. Then the apparatus was evacuated down to 100 mbar absolute and 37 g of ammonia was introduced in gas form over 30 minutes. During the neutralization the reaction vessel was cooled with icewater. Removal of the NH$_4$Cl by filtration yielded 821.7 g of clear filtrate. After distillation of the heptane on the rotary evaporator, this yielded 228.2 g of 97% colorless, highly viscous Hf(O-n-C$_4$H$_9$)$_4$. Melting point: 106° C. The $^{13}$C NMR spectrum is shown in FIG. 4.

EXAMPLE 6

The alcohols listed in Table 1 were reacted similarly to Example 5 with HfCl$_4$ and the orthoesters listed in the Table were obtained with the stated melting points.

TABLE 1

| Alcohol Used | Solvent | Orthoester obtained | Melting Point |
|---|---|---|---|
| Ethanol | Heptane | Hf(OC$_2$H$_5$)$_4$ | 198° C. |
| n-Butanol | Heptane | Hf[O(CH$_2$)$_3$CH$_3$]$_4$ | 106° C. |
| i-Butanol | Heptane | Hf[O—CH(CH$_3$)—C$_2$H$_5$]$_4$ | 142° C. |
| Octanol | Heptane | Hf(O—C$_8$H$_{17}$)$_4$ | −13° C. |

Figure 5:
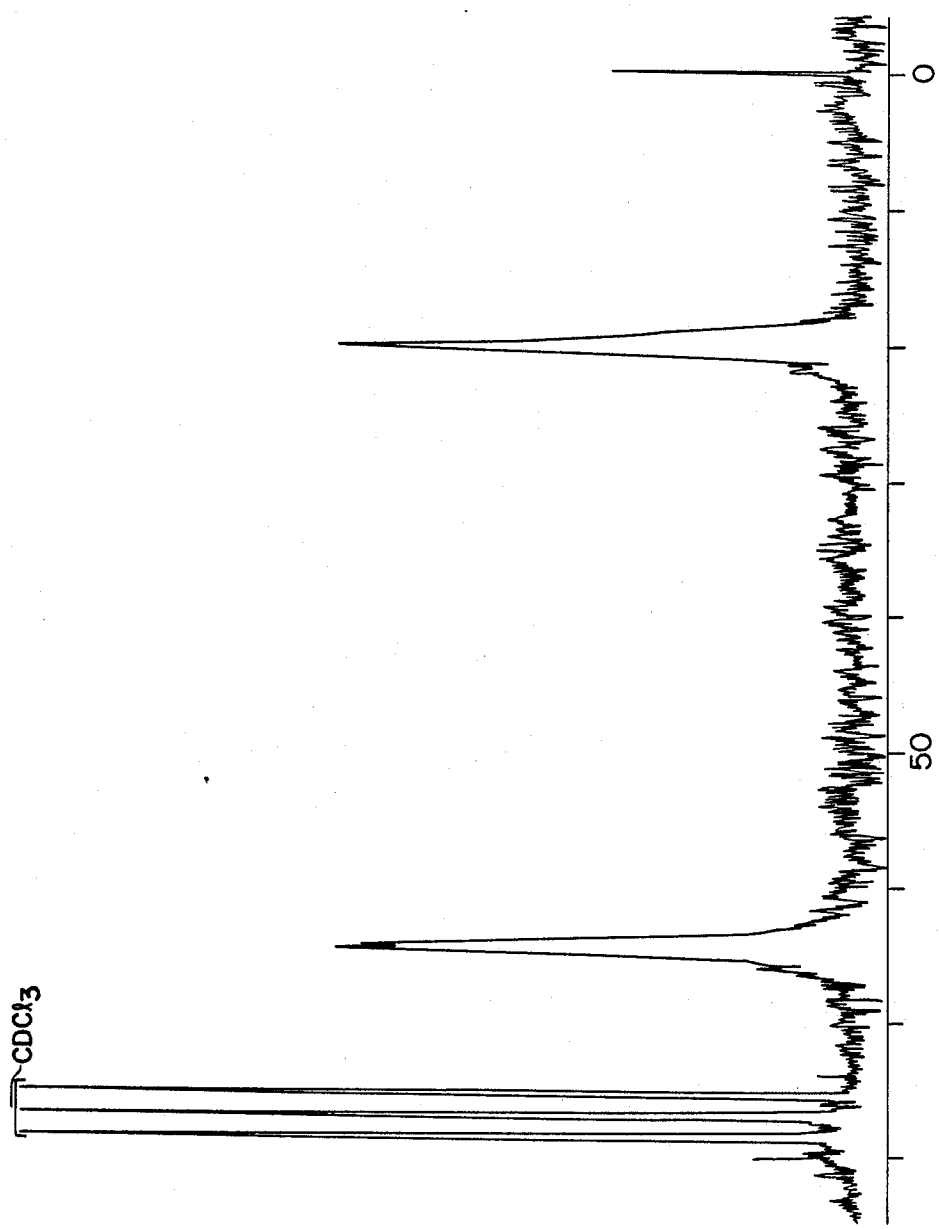
Figure 6:
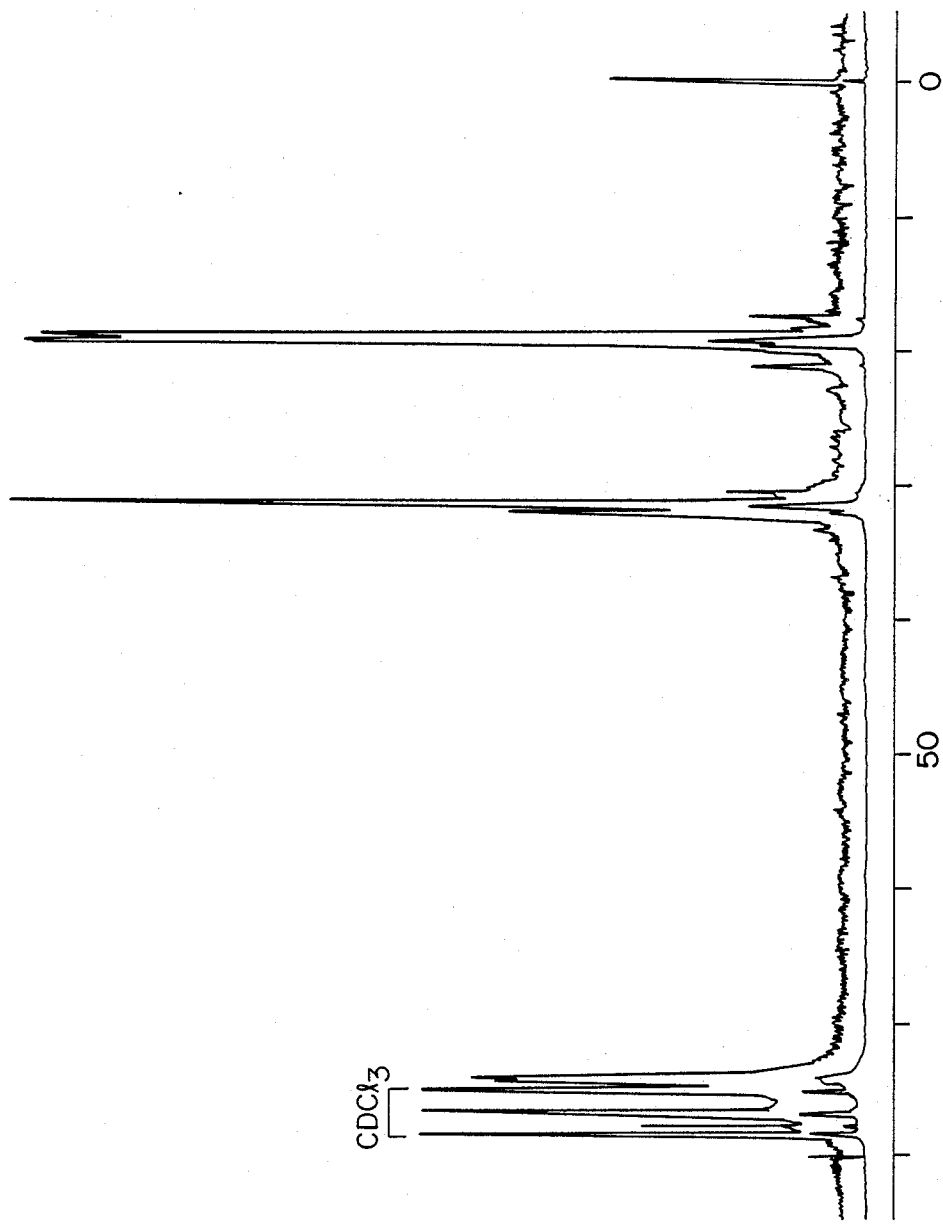
Figure 7:
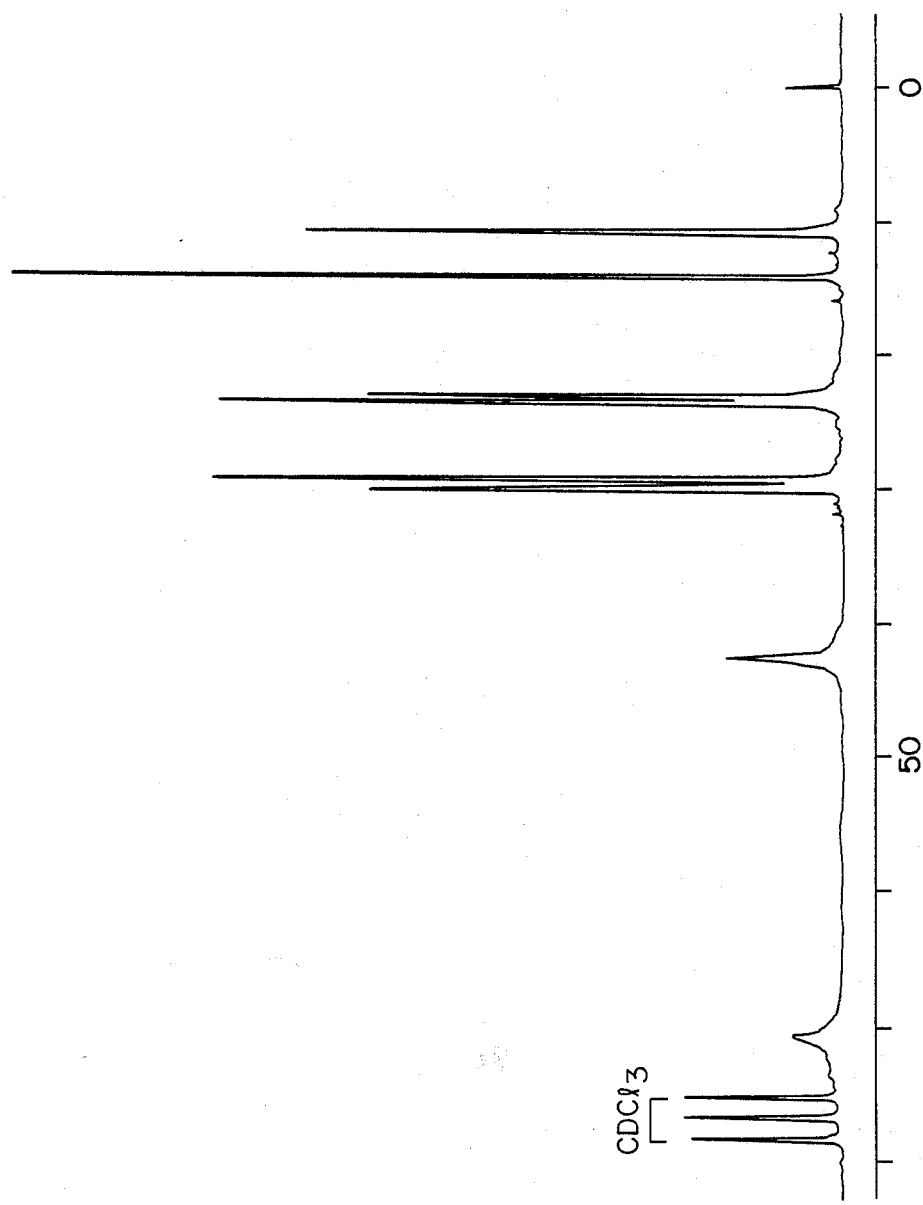

The $^{13}$C NMR spectrum of tetraethylhafnate is given in FIG. 5, that of tetraisobutylhafnate in FIG. 6, and that of tetraoctylhafnate in FIG. 8.

EXAMPLE 7

The examples 1,4 and 5 were repeated with the amounts of methyl cyclohexane, cyclohexane, pentane, decane, toluene, xylene, benzene, carbon tetrachloride, trichlorethylene and chlorobenzene instead of hexane or heptane. The yields of the products, respectively, were as reported in the Examples 1,4 and 5 and the melting points were as reported there. The molecular weights found are listed below.

EXAMPLE 8

Example 4 was repeated with the equivalent amount of a) 2-ethyl-hexanol and (b) n-nonyl alcohol instead of n-propanol. Yields of 98% of (a) tetra (2-ethyl-hexyl) zirkonate of the formula Zr[O—CH$_2$—CN$_2$ (C$_2$H$_5$) C$_4$H$_9$] 4 of the M.P of −33° C. and (b) tetra nonyl zirkonate of the formula Zr (O —C$_9$ H$_{19}$)$_4$ M.P. −2° C. were found.

Referring to the product claims the term "alcohol free" means free of any amount of more alcohol than corresponding to four alkoxy groups per metal atom. Correspondingly, the formula M (OR)$_4$ means that molecular weights were found corresponding to the calculated molecular weight according to the formula M (OR)$_4$ in which exactly four alkoxy groups are bound to every metal atom corresponding to a monomer molecule of one metal atom bound to four alkoxy groups according to the structure of

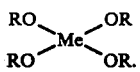

Therein essentially no further alcohol is associated and no metal atoms are connected by oxane bridges to oligomers as reported by BRADLEY et al, J. CHEM. SOC. 1953 pages 2025 to 2030, especially as seen there in formulas FIG. 1 and 2. The molecular weights found are:

| Example | formula | found | calculated |
|---|---|---|---|
| 1 | Zr (O—n-C$_4$H$_9$)$_4$ | 384 | 383 |
| 2 | Zr (O—i-C$_3$H$_7$)$_4$ | 327 | 327 |
| 3 | Zr (O—C$_2$H$_5$)$_4$ | 272 | 271 |
| 4 | Zr (O—n-C$_3$H$_7$)$_4$ | 328 | 327 |
| 5 | Hf (O—n-C$_4$H$_9$)$_4$ | 471 | 470.5 |
| 6 | Hf (O—C$_2$H$_5$)$_4$ | 358 | 358.5 |
|   | Hf (O—n-C$_4$H$_9$)$_4$ | 472 | 470.5 |
|   | Hf (O—i-C$_4$H$_9$)$_4$ | 471 | 470.5 |
|   | Hf (O—C$_8$H$_{17}$)$_4$ | 696 | 694.5 |
| 8 | Zr (O—CH$_2$—CH$_2$(C$_2$H$_5$)C$_4$H$_9$)$_4$ | 609 | 608 |
|   | Zr (O—C$_9$H$_{19}$)$_4$ | 665 | 663 |

It will be understood that the specification and examples are illustrative but not limitative of the present invention and that other embodiments within the spirit and scope of the invention will suggest themselves to those skilled in the art.

We claim:

1. A method for the preparation alcohol-free of an orthoester of the formula $$M (OR)_4 \qquad (I)$$

in which M is selected from the group consisting of zirconium and hafnium and R represents an alkyl or cycloalkyl moiety of 1 to 20 carbon atoms, the method comprising:
reacting a metal halide with an alcohol in a hydrocarbon or chlorinated hydrocarbon solvent wherein the metal is M and the amount of alcohol substantially corresponds with the stoichiometric amount required for formation of the orthoester of formula I to form a reaction mixture containing the orthoester and halogen hydride;
neutralizing the halogen hydride; and
recovering the orthoester.

2. The method of claim 1 wherein the alcohol is introduced into a previously formed suspension of the metal halide in the solvent by means submerged in the solvent.

3. The method of claim 1 wherein the halogen hydride is neutralized by an amine which is added to the reaction mixture.

4. The method of claim 3 wherein the reaction mixture is contained in a reactor vessel, the reactor vessel has a space above the reaction mixture which is evacuated to a partial vacuum and the amine is introduced into the reaction vessel.

* * * * *

UNITED STATES PATENT AND TRADEMARK OFFICE
CERTIFICATE OF CORRECTION

PATENT NO. : 4,891,439
DATED : January 2, 1990
INVENTOR(S) : Udo Horns et al It is certified that error appears in the above-identified patent and that said Letters Patent is hereby corrected as shown below:

Column 3, line 12, delete "as has been proven by".

Column 4, line 20, delete "$_{13}C$" and insert --$^{13}C$--.

Column 4, line 35, delete "wa" should read --was--.

Signed and Sealed this

Sixth Day of April, 1993

Attest:

STEPHEN G. KUNIN

Attesting Officer

Acting Commissioner of Patents and Trademarks